(12) United States Patent
Casutt

(10) Patent No.: US 7,107,883 B2
(45) Date of Patent: Sep. 19, 2006

(54) SCREW-DRIVING TOOL FOR IMPLANT SCREWS

(75) Inventor: Simon Casutt, Gossau (CH)

(73) Assignee: Zimmer GmbH, Winterthur (CH)

( * ) Notice: Subject to any disclaimer, the term of this patent is extended or adjusted under 35 U.S.C. 154(b) by 105 days.

(21) Appl. No.: 10/867,872

(22) Filed: Jun. 14, 2004

(65) Prior Publication Data

US 2004/0255734 A1    Dec. 23, 2004

(30) Foreign Application Priority Data

Jun. 20, 2003    (EP) ................................. 03013952

(51) Int. Cl.
*B25B 23/159* (2006.01)
*B25B 23/14* (2006.01)

(52) U.S. Cl. .................... 81/467; 81/477; 73/862.21

(58) Field of Classification Search ............... 81/467, 81/476, 477, 478, 480; 73/862.21, 862.23, 73/862.321

See application file for complete search history.

(56) References Cited

U.S. PATENT DOCUMENTS

| | | | |
|---|---|---|---|
| 2,151,953 A | 3/1939 | Zimmerman | |
| 2,256,478 A | 9/1941 | Hill | |
| 2,461,491 A | 2/1949 | Booth | |
| 2,607,219 A * | 8/1952 | Millard et al. ........... | 73/862.21 |
| 3,783,682 A | 1/1974 | Lipari | |
| 4,774,864 A * | 10/1988 | Dossier ....................... | 81/474 |
| 5,048,381 A | 9/1991 | Allen et al. | |
| 5,737,983 A | 4/1998 | Rennerfelt | |
| 6,132,435 A | 10/2000 | Young | |
| 6,575,042 B1 | 6/2003 | Rinner | |

FOREIGN PATENT DOCUMENTS

| | | | |
|---|---|---|---|
| DE | 3808238 A1 * | 10/1988 | |
| DE | 4200364 A1 | 9/1993 | |
| EP | 1234637 A2 | 8/2002 | |
| FR | 1386414 A | 1/1965 | |
| WO | WO 00/38589 A | 7/2000 | |

* cited by examiner

*Primary Examiner*—David B. Thomas
(74) *Attorney, Agent, or Firm*—Townsend and Townsend and Crew LLP

(57) ABSTRACT

The invention relates to a screw-driving tool for implant screws having an elongate handle (2) and having a bar-shaped tool which is anchored in the elongate handle (2). An elastic, hollow spiral (10) is provided for the transmission of a predetermined torque, with a bar (3) being guided through the spiral (10) and being fixedly connected to the rotatable side of the spiral and indicating a rotational angle or a torque respectively at the opposite side.

14 Claims, 2 Drawing Sheets

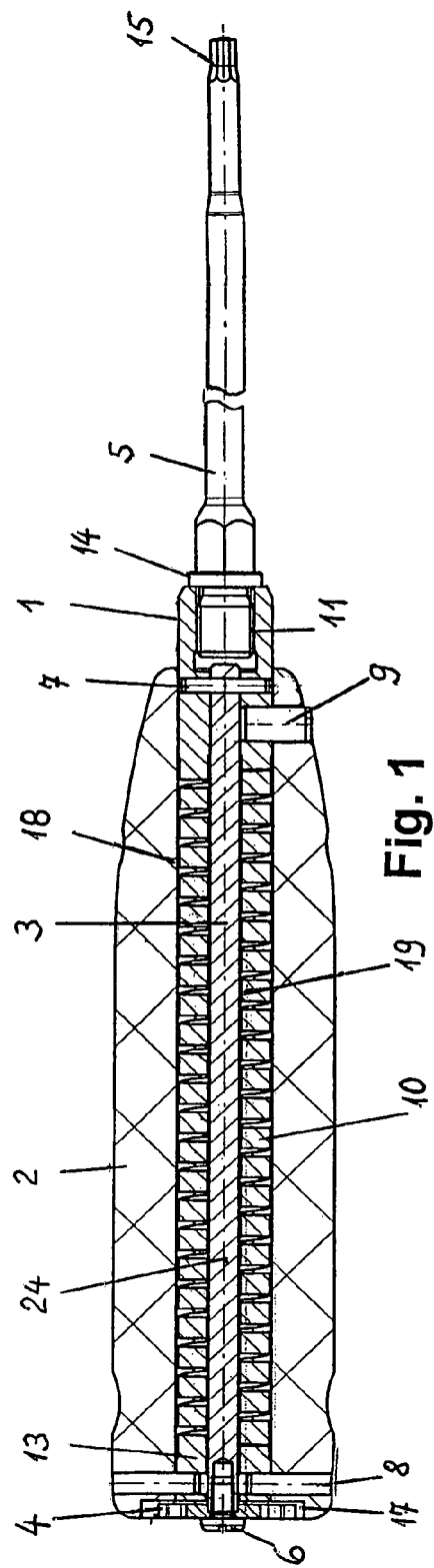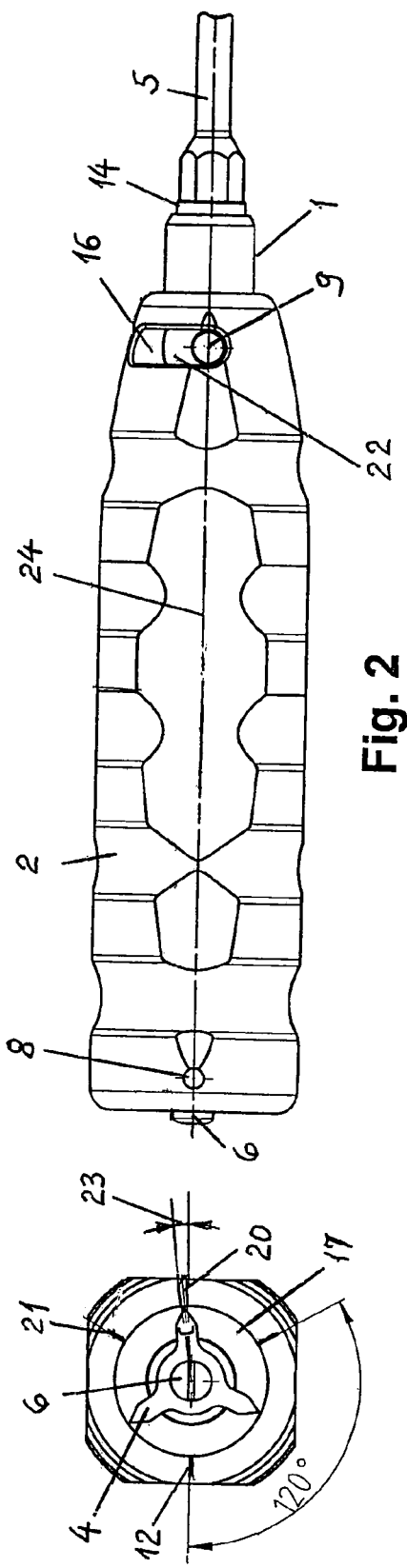

SCREW-DRIVING TOOL FOR IMPLANT SCREWS

BACKGROUND OF THE INVENTION

The invention relates to a screw-driving tool for implant screws having an elongate handle and having a bar-shaped tool which is anchored in the elongate handle.

Implant screws of a specific size may as a rule only be tightened with a limited torque for the connection of implant parts so that the thread or the pressed-together implant parts are not damaged. On the other hand, an implant screw must be tightened with a minimum torque so that it does not become loose. The manufacturer of implants which can be screwed in should therefore provide the possibility of carrying out such a screw connection while observing a predetermined torque. Tools for the screwing in of such screws should be capable of being easily sterilized and should show no wear due to their multiple use. A screw-driving tool which has a torque measurement and is licensed for non-sterile areas is shown in U.S. Pat. No. 5,048,381. U.S. Pat. No. 5,737,983 likewise shows general screw-driving tools with a torque bar which is limited against overload in its movement so that this limit can be felt in a tactile manner as a resistance in order to have reached a minimum torque with certainty. In contrast to the technical screw connections, in which a minimum tightening torque against the loosening of the screw connection is required, a certain tightening torque may not be exceeded with an implant screw. An overloading which is not controlled as it rises is therefore the same as a limit for the screwing in of an implant screw as the subjective feeling on the screwing in with a normal screwdriver. This is where the invention comes into play. Its object is to make the reaching of a permitted screwing torque known to the operating physician with certainty.

SUMMARY OF THE INVENTION

It is therefore an object of the present invention to provide an elastic spiral for the torque transmission which is secured at a foot part in the elongate handle, is rotatably journalled in the elongate handle at a head part and opens into an actual tool part, with the spiral being hollow and a bar being guided through the spiral which is fixedly anchored in the head part and is rotatably journalled in the foot part in order to indicate the relative rotation and the torque between the tool part and the elongate handle outside the foot part by a pointer.

Such a tool has the advantage that a larger indicating angle for an applied torque is possible in comparison with a torsion bar limited to the handle. A screw-shaped hollow spiral represents a substantially larger energy store with an equally large torque, i.e. a larger angle of rotation is created with a smaller specific load, with the hollow spiral also still being accommodated in a relatively small space appropriate for the handle. Basically, a softer torsion spring is created which, however, can be actuated over a large angular range without local stress peaks which are too large. It can only be recognized by a theoretical unwinding of the screw-shaped spiral that much more length for an elastic bending deformation is available here, with the same bending torque occurring in each cross-section. The direction of rotation of the spiral corresponds to the direction of rotation of the screw thread when an implant screw is screwed in. On the screwing in, the spiral will therefore reduce its diameter and also exert forces in the axial direction. For this reason, it is expedient to provide the head part movable in the direction of rotation with an axial latch which acts in both directions relative to the elongate handle. Such an axial latch also prevents a springing back when the screw-driving tool is placed onto an implant screw.

With an abutment in the handle part, a rotation of the head part can be restricted which lies well beyond the provided torque which can be indicated by a pointer, and thus a plastic deformation of the hollow spiral can be prevented. The restriction can take place at a pin or screw connected to the head part and extending in a slot of the handle part. A slot with an angle of rotation between 30° and 90° results in a display range for a permitted torque which is reasonable for practice, and this angle can be produced with one hand at the handle without repositioning. When the tool part is releasably coupled to the head part, different tool parts and handles having differently sized torque indicators can be combined with one another in a modular kit. When the elongate handle consists of a plastic which can be sterilized, such as is usual with instrument holders, and when the remaining parts are made of metal, for example of non-rusting metal alloys, sterilization of the whole is possible.

The spiral can be designed with a dual thread as a double helix for the symmetrical distribution of force. The head part, the spiral and the foot part can be made in one piece, whereby further incorrect joint positions and potential error sources are avoided.

When, as described above, a relatively large angle is available for the reading off of the torque, not only the reading is very precise, but a tolerance field for the zero position can also be attached at the zero position at which it can be recognized whether the zero position has become displaced, for example due to overloading in the unsecured state, i.e. without using the above-described abutment. The larger the display angle for a permitted torque, the larger the tolerance range for the zero position that can also be selected. With an angle of rotation of 60°, the zero position can, for example, have a tolerance of plus/minus 2°, which corresponds to a control range which is still easily visible.

The invention will be described in the following with reference to embodiments.

BRIEF DESCRIPTION OF THE DRAWINGS

FIG. 1 shows a screw-driving tool in accordance with the invention in a longitudinal section;

FIG. 2 is a side view of the tool in FIG. 1;

FIG. 3 is a plan view of the rear part of the tool of FIG. 2;

DESCRIPTION OF THE PREFERRED EMBODIMENTS

Figure 4:
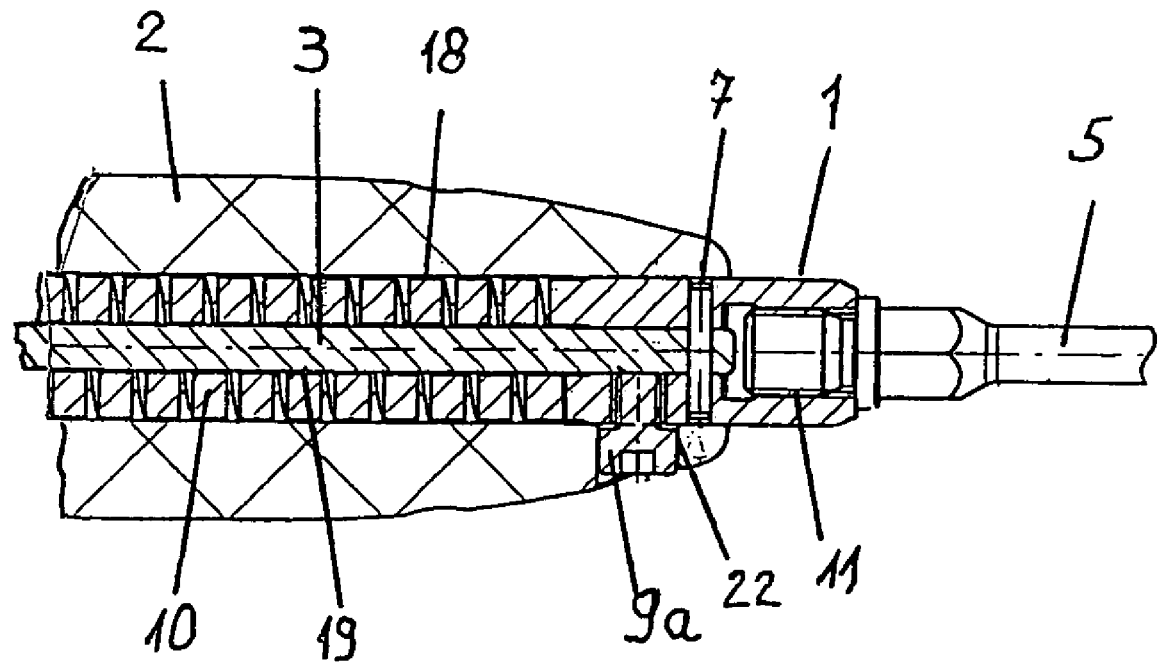
FIG. 4 is a section of FIG. 1 with a screw for securing in the direction of rotation and in the axial direction.

FIGS. 1, 2 and 3 show a first embodiment of a screw-driving tool in accordance with the invention. A tool part 5, which ends in a hexagon head 15, is indirectly connected to an elongate handle 2. A spiral 10 acts as an intermediate member and ends toward the tool part 5 in a head part 1 which is rotatably journalled in the elongate handle 2. The spiral ends at the other end in a foot part 13 which is rigidly connected to the elongate handle 2 via two pressed-in cylindrical pins 8.

A bar 3 is guided through the spiral 10 which is hollow in design and is in turn rigidly anchored in the head part 1 by a pressed-in cylindrical pin 7. The bar 3 is rotatably journalled in the foot part 13 and projects out of the foot part 13 so that a pointer 4 can be fastened thereto by a fastening screw 6. Clearance 18 is present between the spiral 10 and the elongate handle 2 which prevents the spiral from jamming when it enlarges its diameter during resilient dilation. Clearance 19 is provided between the spiral 10 and the bar 3 which prevents the spiral 10 from seizing when compressing on the bar 3. A radial pin 9 is pressed into the head part 1 for the absorption of an axial force between the head part 1 and the elongate handle 2 and is guided at both sides in a slot 22 extending transversely to the longitudinal axis 24 and allows a rotational movement up to an abutment 16. The axial forces to be absorbed tend to be low. They arise on the placing of the hexagonal head 15 onto a screw and on the compressing and opening of the screw-shaped spiral 10.

The tool part 5 is exchangeably screwed together with the head part 1 via a thread 11 and sits at a shoulder 14 on the head part 1. Different tools for a predetermined torque can be used in this manner.

It can be recognized in FIG. 3 that the indicator 4 is made in triplicate at intervals of 120° and that indicator 12 for a desired torque 21 is likewise made in triplicate at intervals of 120° in order to allow a reaching of the desired torque to be read off from different directions. One of the three pointers is marked by a "C" and, in its zero position 20, is opposite a marked tolerance angle 23 which indicates a permitted deviation of the zero position.

As seen in FIG. 2, the radial pin 9 is almost at the end of the slot 22 in the zero position. If the elongate handle is now turned to the right in the clockwise direction, after the tool part 5 has encountered resistance in the direction of rotation, the elongate handle, with its indicator 12, rotates with respect to the head part 1 and thus also with respect to the pointer 4. The torque can now be increased until the marked desired torque 21 has been reached. The pointer 4 is let into a recess 17 at the end of the elongate handle 2 so that it is protected against mechanical damage.

A further example is shown in FIG. 4 which differs from FIG. 1 only in that the pressed-in radial pin 9 has been replaced by a screw 9a. If the pressed-in cylindrical pins 8 (FIG. 2) are now also replaced by reamed pins, which can be released again, the elongate handle 2 can be pulled off to the front in the direction of the axis 24 after the removal of the reamed pins and of the screw 9a, which allows better cleaning.

Figure 5:
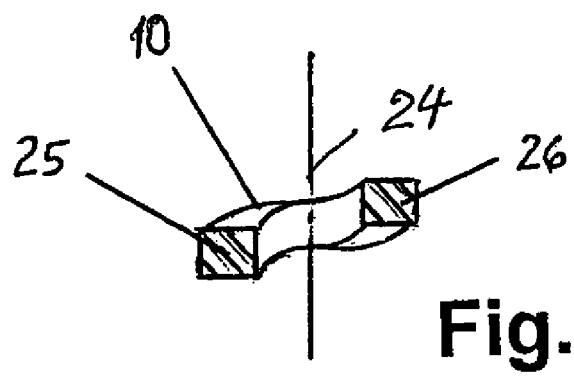
FIG. 5 is a section through a section of a hollow spiral.

FIG. 5 shows a half turn of the spiral 10 with the cross-sections 25, 26. With respect to the axis 24, the same bending torque occurs in each cross-section 25, 26 with torsion. With a length of the elongate handle 2 limited by practice, an angle of rotation of, for example, 60° arises by the substantially larger unwound length of the hollow spiral used as the torsion spring for a predetermined torque. For example, the unwound length of the hollow spiral 10 can correspond to 1.4 times the length of the elongate handle 2. An angle of rotation of this magnitude makes it possible to observe a predetermined torque very precisely and also to carry out a relatively precise control of the zero position. A torsion bar restricted to the length of the elongate handle would only allow a minimum rotation with a corresponding unreliability in the reading with an equally limited maximum specific load.

The invention claimed is:

1. A screw-driving tool for implant screws having an elongate handle and having a bar-shaped tool which is anchored in the elongate handle, wherein an elastic spiral is provided for the torque transmission which is secured at a foot part in the elongate handle, is rotatably journalled at a head part in the elongate handle and opens into an actual tool part, with the spiral being hollow and a bar being guided through the spiral which is fixedly anchored in the head part and is rotatably journalled in the foot part in order to indicate the relative rotation and the torque between the tool part and the elongate handle outside the foot part by a pointer, the spiral being made in one piece with the head part and the foot part.

2. A screw-driving tool in accordance with claim 1, wherein the head part is provided with an axial latch acting in both directions relative to the elongate handle.

3. A screw-driving tool in accordance with claim 1, wherein the handle part has an abutment for a limited angle of rotation of the head part.

4. A screw-driving tool in accordance with claim 3, wherein a projecting radial pin is anchored in the head part and is restricted in its pivotal movement and in the axial direction by a slot in the elongate handle.

5. A screw-driving tool in accordance with claim 3, wherein a projecting screw is anchored in the head part and is restricted in its pivotal movement and in the axial direction by a slot in the elongate handle.

6. A screw-driving tool in accordance with claim 4, wherein the slot is provided for an angle of rotation between 30° and 90°.

7. A screw-driving tool in accordance with claim 1, wherein the tool part is releasably coupled to the head part.

8. A screw-driving tool in accordance with claim 1, wherein the elongate handle consists of a plastic which can be sterilized.

9. A screw-driving tool in accordance with claim 1, wherein the spiral is made as a double helix.

10. A screw-driving tool in accordance with claim 1, wherein, in a zero position for the rotation of the pointer, a tolerance angle at the handle part marks whether the zero position still lies within a permitted limit.

11. A screw-driving tool in accordance with claim 10, wherein the tolerance angle amounts to more than plus/minus 2°.

12. A screw-driving tool in accordance with claim 1, wherein the spiral in its unwound length is longer than the elongate handle.

13. A screw-driving tool in accordance with claim 1 wherein the spiral, the head part and the foot part comprise a one-piece tubular member of unitary construction having a circumferential wall defining a hollow interior, the circumferential wall defining the head part and the foot part, a portion of the wall intermediate the head part and the foot part being spiral slit across a width of the wall relative to one of the bar and the handle for indicating relative angular displacement between the bar and the foot end when a torque is applied to the handle and therewith to the tubular member.

14. A screw-driving tool for implant screws comprising a handle, a one-piece tubular member of unitary construction made of an elastically deformable material and having a circumferential wall defining a hollow interior, the circumferential wall including a head end adapted to receive an actual tool and a foot end, a portion of the wall intermediate the ends being spirally slit across a width of the wall, the foot end being non-rotatably connected to the handle and the head end being rotatable relative to the handle, a bar extending longitudinally through the hollow interior, the bar being fixedly secured to the head end and journalled in the foot end, and a pointer located proximate the foot end of the tubular member and non-rotatable relative to one of the bar and the handle for indicating relative angular displacement between the bar and the foot end when a torque is applied to the handle and therewith to the tubular member.

* * * * *